United States Patent
Claessens

(10) Patent No.: US 9,023,305 B2
(45) Date of Patent: May 5, 2015

(54) STRONTIUM-82/RUBIDIUM-82 GENERATOR, METHOD FOR PRODUCING A RUBIDIUM-82 COMPRISING DIAGNOSTIC AGENT, SAID DIAGNOSTIC AGENT AND ITS USE IN MEDICINE

(75) Inventor: Roland Anthonius Maria Johannus Claessens, Milsbeek (NL)

(73) Assignee: Stichting Jeroen Bosch Ziekenhuis, s'-Hertogenbosch (NL)

( * ) Notice: Subject to any disclaimer, the term of this patent is extended or adjusted under 35 U.S.C. 154(b) by 630 days.

(21) Appl. No.: 13/056,103

(22) PCT Filed: Aug. 14, 2009

(86) PCT No.: PCT/EP2009/060584
§ 371 (c)(1),
(2), (4) Date: Apr. 15, 2011

(87) PCT Pub. No.: WO2010/020596
PCT Pub. Date: Feb. 25, 2010

(65) Prior Publication Data
US 2011/0182808 A1    Jul. 28, 2011

(30) Foreign Application Priority Data
Aug. 18, 2008  (EP) .................... 08075710

(51) Int. Cl.
*C01D 17/00*   (2006.01)
*C01F 11/00*   (2006.01)
*G21G 1/00*    (2006.01)
*A61K 51/12*   (2006.01)

(52) U.S. Cl.
CPC ............ *G21G 1/001* (2013.01); *A61K 51/1282* (2013.01); *G21G 1/0005* (2013.01); *G21G 2001/0031* (2013.01)

(58) Field of Classification Search
CPC ................................ C01D 17/00; C01F 11/00
USPC ..................... 424/1.11, 1.69; 423/2, 249, 598
See application file for complete search history.

(56) References Cited

U.S. PATENT DOCUMENTS

| 4,406,877 A   | * | 9/1983  | Neirinckx et al. ........... 424/1.61 |
| 5,885,216 A   | * | 3/1999  | Evans et al. .................... 600/431 |
| 5,966,583 A   | * | 10/1999 | Taylor et al. ...................... 423/2 |
| 2007/0140958 A1 |   | 6/2007  | Dekemp |

FOREIGN PATENT DOCUMENTS

| WO | 2004105049 | 12/2004 |
| WO | 2006135374 | 12/2006 |

OTHER PUBLICATIONS

"Experience with a 82Sr/82Rb Generator for Clinical Use," Kensett, M., et al., Appl. Radiat. Isot. 38(3): 227-231 (1987).*
M.J. Kensett et al., Experience with a 82Sr/82Rb Generator for Clinical Use, Appl. Radiat. Isot. vol. 38(3), 227-231, 1987.*
A. Cappiello et al., New Materials and Packing Techniques for Micro-HPLC Packed Capillary Columns, Chromatographia, vol. 32 (7/8), 389-391, 1991.*

* cited by examiner

*Primary Examiner* — Michael G Hartley
*Assistant Examiner* — Jagadishwar Samala
(74) *Attorney, Agent, or Firm* — Bret E. Field; Benjamin C. Pelletier; Bozicevic, Field & Francis LLP

(57) ABSTRACT

The invention relates to a strontium-82/rubidium-82 generator, comprising a column filled with a cationic exchanger loaded with strontium-82, and having an inlet and an outlet, and a liquid medium, wherein parts of the column, inlet and outlet coming into contact with the liquid medium are iron-free, preferably metal-free, to a method for producing rubidium-82, and to the obtained diagnostic agent.

14 Claims, 6 Drawing Sheets

STRONTIUM-82/RUBIDIUM-82 GENERATOR, METHOD FOR PRODUCING A RUBIDIUM-82 COMPRISING DIAGNOSTIC AGENT, SAID DIAGNOSTIC AGENT AND ITS USE IN MEDICINE

The present invention relates to a strontium-82/rubidium-82 generator, to a method for producing a rubidium-82 comprising diagnostic agent using such strontium-82/rubidium-82 generator, to the diagnostic agent obtainable therewith, and to the use of this diagnostic agent in medicine.

In nuclear medicine conventional diagnostic techniques are applied for coronary artery disease imaging and for the determination of the severity of the disease. Diagnostic agents used for the determination of myocardial perfusion comprise thallium-201 or technetium-99 m. However, these diagnostic agents are limited in use by the occurrence of attenuation artefacts and do not permit an accurate estimation of extension and severity of coronary artery disease.

These drawbacks make rubidium a better choice as a potassium-analog. Rubidium-82 is suitable for positron emission tomography, because Rubidium-82 is a positron emitter rendering higher quality images than conventional gamma camera imaging. Moreover Rubidium-82 is a radionuclide with an ultra-short half-life ($t_{1/2}$=75s). This ultra-short half life allows high doses at short imaging times but urges production of rubidium-82 near the patient.

Presently, a strontium-82/rubidium-82 generator comprises a generator column assembly comprising adaptors with nuts and ferrules, a column and two micro filters. The generator column is about 2.6 cm in length, 6 mm internal diameter and has a 0.5 mm wall thickness. All components are made of stainless steel type 316. The cationic exchanger may be α-hydrous tin oxide loaded with about 50 mCi strontium-82. The liquid medium in the strontium-82 loaded cationic exchanger is physiological 0.9% sodium chloride. Sterile and pyrogen free 0.9% sodium chloride is also used as elution medium.

This known strontium-82/rubidium-82 generator may be used for several days to several weeks. However, the known generator is not sufficiently stable for use during an extended period of time. Such stability is determined by a so-called breakthrough of strontium-82 during elution. An early breakthrough of strontium-82 blocks the possibility of reloading the cationic exchanger with strontium-82 for a continued production of the rubidium-82 diagnostic agent. Furthermore, using a generator for an extended period of time requires a method of sterilization of it.

Further research revealed that by using a physiological buffer having a pH of 6-8.5 as an elution medium for rubidium-82, the stability of the strontium-82/rubidium-82 generator can be substantially improved. A substitution of the physiological 0.9% sodium chloride elution medium by a physiological buffer having a pH of 6-8.5 as such is not recommendable in relation to the daily use of the generator. In particular, after use of a sterilization medium in the form of hypochlorite solution it turned out that a gelatinatious material is formed jeopardizing the functionality of the strontium-82/rubidium-82 generator, in particular because the column filters become clogged and ultimately blocked.

The present invention is based on the insight that a strontium-82/rubidium-82 generator having parts coming into contact with the liquid medium, which part has been made of iron-free and preferably of metal-free material, that such clogging gelatinatious material is not formed and the generator has the desired improved stability and may be reloaded with strontium-82 several times without any significant breakthrough of strontium-82. At the same time, optimal performance and sterility are maintained. The continued use of the strontium-82/rubidium-82 generator and the option of reloading without significant strontium-82 breakthrough results in an extended operation time period before the generator is to be recycled and the cationic exchanger renewed and subsequently loaded again with strontium-82. This results in an extensive reduction in costs.

For instance, a generator according to the invention may be used over an extended period of time such as 2-6 months at substantially constant stability.

Accordingly, the present invention provides a strontium-82/rubidium-82 generator, comprising a column filled with a cationic exchanger loaded with strontium-82, and having an inlet and an outlet, and a liquid medium, wherein parts of the column, inlet and outlet coming into contact with the liquid medium are iron-free, preferably metal-free.

This strontium-82/rubidium-82 generator according to the invention is suitable for elution with a physiological buffer having a pH of 6-8.5 and for sterilization using a hypochlorite solution, without the occurrence of deteriorating clogging and ultimately blocking of the generator due to the formation of gelatinatious material. Without being bound to any theory, it might be that the gelatinatious material formed comprises a water insoluble iron salt. Iron likely originates from the metallic parts of the generator and the counter ions such as phosphate, originate from the elution medium being a physiological buffer, for instance a phosphate buffer saline solution having a pH of 7.2-7.4.

It is possible that the strontium-82/rubidium-82 generator during storage, transport or out of use for other reasons, may comprise a liquid medium other than the elution medium according to the invention. But, for elution and for maintaining the extended stability, it is required according to the invention that the elution medium for rubidium-82 is a physiological buffer having a pH of 6-8.5. The lower limit for the pH is selected such as to allow to an acceptable extent such as per volume, the elution of rubidium-82 from the cationic exchanger. Accordingly, the lower is the pH, the better is the rubidium-82 elution. However, due to the very short half time of rubidium-82, it is required that the elution medium is almost directly to be administered by for instance intravenous injection into the patient. Preferred is therefore a physiological buffer having a pH in the range of 7-8 and more preferably in the range of 7.2-7.4. A physiological buffer involves that the osmolarity of the buffer is selected such that the injection into a patient will not result in any adverse effects, taking into account a volume to be injected of about 2-30 ml at a rate of about 10-80 ml/minute.

Suitable physiological buffers comprise citrate/sodium hydroxide buffer, citrate/phosphate buffer, borate/hydrogen chloride buffer, boric acid/sodium hydroxide buffer, Tris buffer, veronal/HCl buffer and piperazine/sodium hydroxide buffer. Preferred physiological buffers are carbonate buffers, phosphate buffers and Tris buffers.

In order to avoid any leaching of metal from the generator, the part of column, inlet and outlet inclusive ferrules, tubings and the like are to be made of iron-free and preferably metal-free material or coated with metal-free material.

Metal-free means in particular iron-free. Accordingly, it is possible that the column, inlet and outlet or any generator elements may be made of an iron-free metal, such as titanium. However, in the alternative it is preferred that the relevant parts of the column inlet and outlet coming into contact with the liquid medium are made of less expensive metal-free material. A suitable metal-free material is a plastic such as PEEK or Teflon. PEEK material is preferred because PEEK material is already used for columns, inlet and outlet within the HPLC chromatography technique. Such plastic material is of lower costs than iron-free metal material suitable for use in the generator.

In order to guarantee that the rubidium-82 produced as a diagnostic agent with the strontium-82/rubidium-82 generator is suitable for human use intravenously it is mandatory that the generator is frequently, and when needed, sterilized using a sterilization medium. Such sterilization medium is preferably hypochlorite solution of suitable concentration. Hypochlorite has the advantages of a broad anti-bacterial and anti-viral spectrum, relatively easy removal by washing from the generator, and a low detection level. Prior to use this sterilization medium has to be exchanged for either a storage and transportation medium, or directly with the physiologically buffer intended as the elution medium.

A full operation generator assembly for generating and producing the rubidium-82 diagnostic agent in the direct presence of a patient is feasible when the generator comprises
i) a source for the physiological elution buffer;
ii) a source for the sterilisation buffer;
iii) a pump for connecting and transporting the sources to the inlet of the column;
iv) a dose calibrator connected to the outlet of the column; and
v) a patient administration line connected to the dose calibrator.

Such generator is a full service generator for elution, sterilization, and application to the patient and for measuring the radioactive dose generated and a continuous survey of a possible breakthrough of strontium-82. With such full service generator it is preferred that the generator is arranged on a mobile vehicle, such as it is easily transportable between the storage, the radiopharmacy laboratory and the diagnostic room.

It is noted that any cationic exchanger may be used as long as rubidium-82 is selectively eluted. A suitable material is tin oxide, such as a$\alpha$-hydrous tin oxide ($Sn_2O.xH_2O$; x=1-2) or $\alpha$ stannic acid.

Another aspect of the present invention relates to the production of rubidium-82. This method comprises the use of the afore mentioned strontium-82/rubidium-82 generator according to the invention and to elute the generator with the elution buffer being a physiological buffer having in general a pH of 6-8.5, preferably a pH of 7-8 and more preferably of 7.2-7.4. Accordingly, this rubidium-82 diagnostic agent is essentially characterized by the presence of this well defined elution buffer.

As discussed here and above, the methods of the present invention allow the sterilization of the strontium-82/rubidium-82 generator using a sterilization buffer, preferably in the form of a hypochlorite solution. Accordingly, the sterilization of the generator is guaranteed as well as the sterile and pyrogen free character of the rubidium-82 produced therewith.

A last aspect of the present invention relates in particular to the diagnostic agent being in the form of a solution with the elution buffer being the afore mentioned physiological buffer having a pH of 6-8.5. Such diagnostic agent is suitable for use in medicine such as for myocardial perfusion imaging.

Mentioned and other features and advantages of the generator, its production process and its use as a diagnostic agent will be further illustrated in the description of the drawings and the example which follow and which are given for illustrative purposes without the intention to limit the present invention to any extent.

FIG. 1 is a schematic illustration of the rubidium-82 generator in the form of a full surface generator suitable for direct application to a patient;

FIG. 2 shows the activity of strontium-82 (Bq) in the eluate per 37 MBq rubidium-82, the maximum allowable ratio of Sr-82/Rb-82 is about 750 (ppm); and FIG. 3 shows the activity of strontium-85 (Bq) in the eluate of the generator per 37 MBq rubidium-82. The maximum ratio Sr-85/rubidium-82 is about 7500 ppm.

Figure 1:
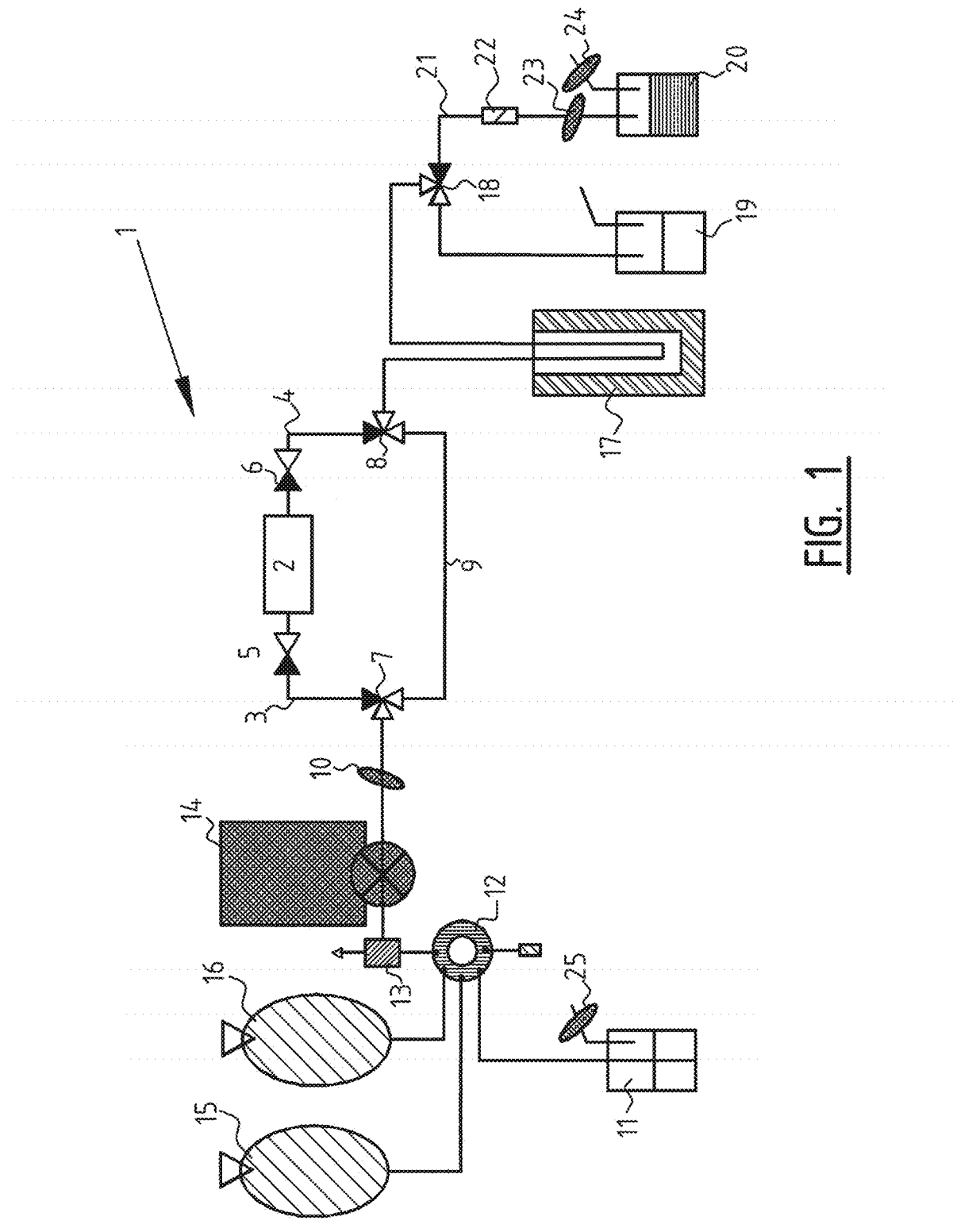

FIG. 1 shows a strontium-82/rubidium-82 generator 1 according to the invention. The generator 1 comprises a column 2 made of PEEK. The column has the following dimensions (length 5.0 cm, internal diameter 0.75 cm, wall thickness 3.25 mm). The column 2 is loaded with 4 grams $\alpha$stannic acid (particle size 75-150 μm) in 0.1 N ammonium chloride buffer. The column 2 is washed with 0.1 N ammonium chloride (pH 10). Subsequently, the column is washed with 2 M sodium chloride and with 0.05% hypochlorite solution. The inlet 3 and the outlet 4 are provided with a valve 5 and 6. The inlet 3 is connected to a multi-valve 7 and the outlet 4 to a multi-valve 8. A bypass 9 extends between the multi-valves 7 and 8 which allows transporting liquid medium through the generator 1 while bypassing the column 2.

Strontium-82 (>25 mCi Sr-82/mg Sr, Sr-85/Sr-82<5, Rb-83/Sr-82<0.15; Rb-84/Sr-82<0.15; Sr-83/Sr-82<0.0015; other nuclides/SR-82<0.01) was neutralized with 0.5 ml 0.5 M Tris buffer (pH 7.5). After the addition of 3.5 ml physiological buffered saline, the mixture was applied via a milipore filter (22 μm) on the column 2. Subsequently, the column 2 is washed with phosphate buffered saline pH 7.4 (8.2 g sodium chloride, 3.1 g $Na_2HPO_4.12H_2O$ and 0.3 g $NaH_2PO_4.2H_2O$ from the container 15.

The 0.05% hypochlorite solution was applied from a container 11 via a multi-valve 12, an air bubble trap 13, the peristaltic pump 14, the filter 10 and then via the valve 7 and 5 to the column 2. It is noted that the tubings are made of PEEK tubings. The column filters (not shown) are 10 μm titanium filters or metal filter holders coated with PEEK or Teflon coating. The sterile filters are Millex Millipore 0.22 μm membrane filters, diameter 25 mm.

Prior to use for patients, the generator 1 is flushed with physiological buffered saline originating from the container 15 until the eluate does not color a 10% potassium iodide solution. Subsequently, the phosphate elution buffer (pH 7.4) is applied from the source 16 through the column 2. The eluate comprising rubidium-82 is passed through a dose calibrator 17 calibrated for rubidium-82 measurement.

Figure 2:
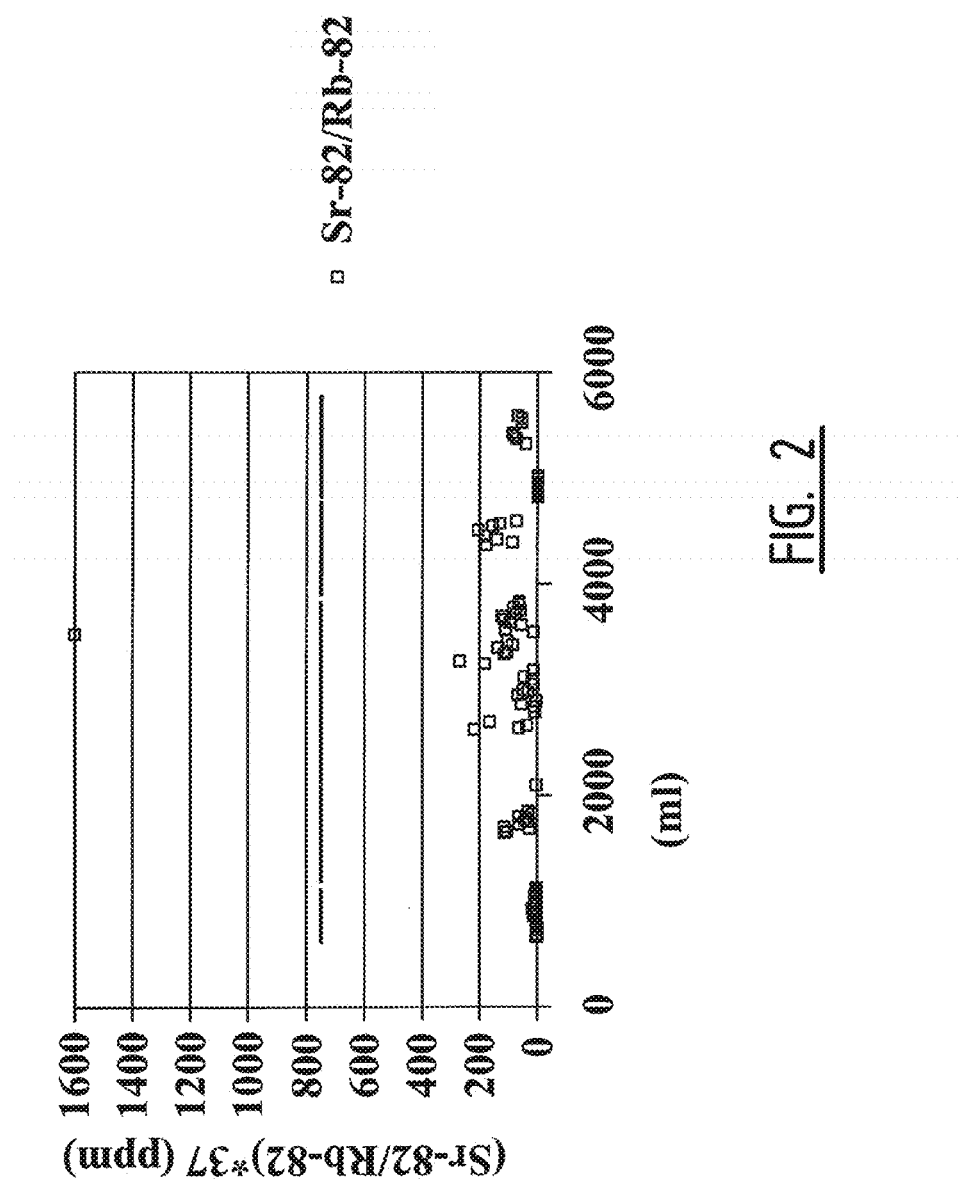

FIG. 2 shows the activity of strontium-82 in the eluate of the column 2 dependent on the elution volume. Clearly, the maximum allowable ratio of SR-82/RB-82 (about 750 ppm) was never surpassed except for one occasion which occurred after the third reload of the column 2 with strontium-82. During testing a large amount of air was introduced on the column 2. In an attempt to remove this air the increased leakage of strontium-82 occurred. After normalization the ratio SR-82/RB-82 remained far below the maximum allowable value over several reloads of the same column 2.

The dose calibrator 17 is connected via a multi valve 18 with either a waste container 19 or to a valve 20 for subsequent administration to the patient. However, the tubing 21 could be disconnected at the connection 22 and directly used for administration to the patient.

Filters 23, 24 and 25 guarantee sterile manipulation of the generator 1.

The measuring mode of the dose calibrator 17 is the integral mode. Accordingly, after the desired dose of strontium-82 is eluted from the column 2 the valves towards the column 2 are closed and elution medium is transported via the bypass tube 9 for flushing the system.

After a waiting time of about 5 minutes a subsequent elution and generation of a new strontium-82 diagnostic agent dose is possible.

After use the system is sterilized by flushing from the container 11 the 0.05% hypochlorite solution. The generator 1 may be stored in the hypochlorite solution or in physiological buffered saline or in the elution buffer.

The diagnostic agent comprising rubidium-82 in the physiological buffer having a pH of 6-8.5 showed during myocardial perfusion imaging with positron emission tomography with better imaging quality at lower radiation exposure to patient. The function of the heart could be determined under rest and stress with an in between waiting time of about 6 minutes for applying the adenosine or dobutamine infusion as a stress generating agent.

Figure 3:
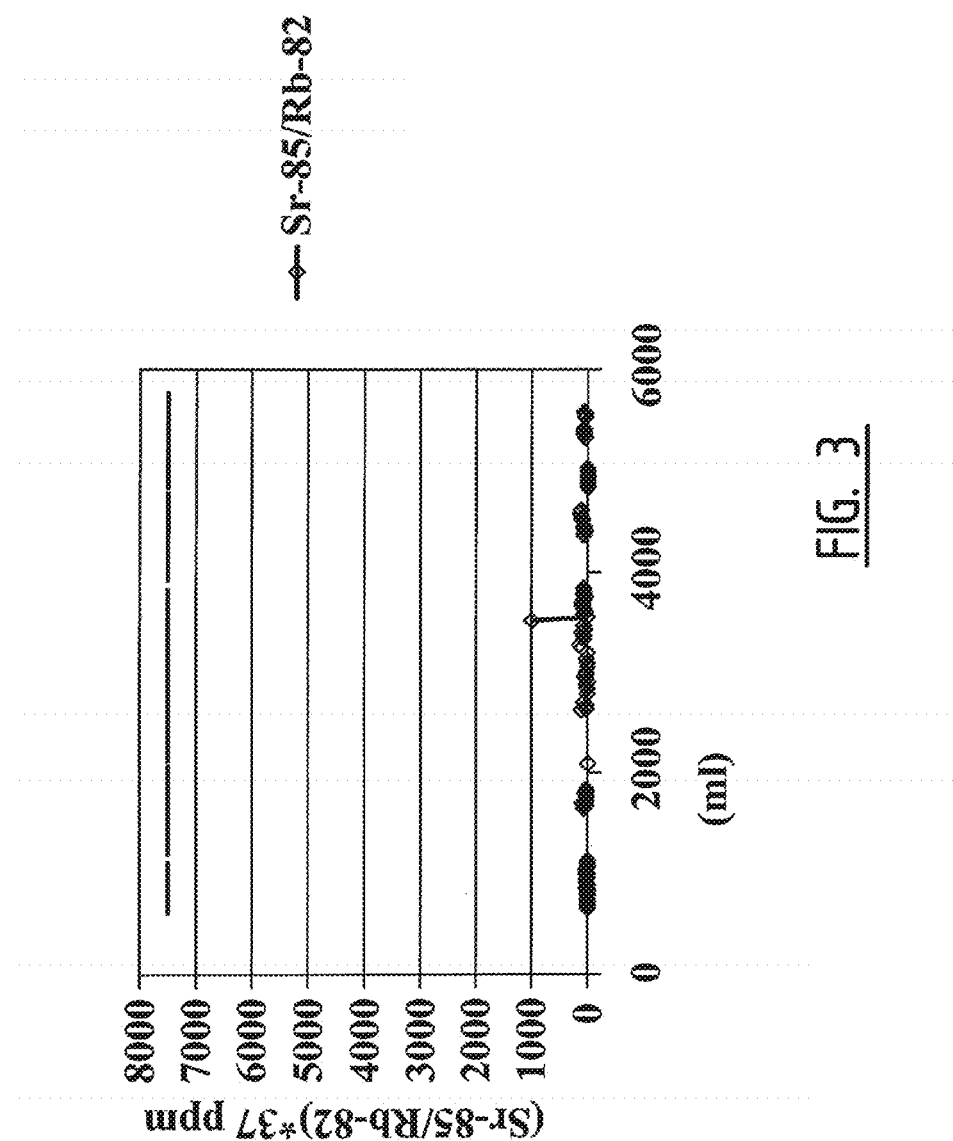

FIG. 3 shows the activity of strontium-85 (Bq) in the eluate of the generator per 37 MBq rubidium-82. The maximum ratio SR-85/rubidium-82 is about 7500 ppm. The activity of strontium-85 is well below the maximum of the ratio of Sr-82/Rb-82.

The increased stability of the strontium binding to the carrier material (hydrous stannic oxide) is obtained by increasing the pH to a value of 7.4 by means of a phosphate buffered saline, used as elution fluid. This increased stability allows an extended period of use of the generator of at least 3 supplementary months as compared to commercially available generators which have to be replaced each month. The generator can be refilled every 4 weeks reducing the costs for strontium-82 significantly.

EXAMPLE

In order to illustrate the contamination of generator eluates with Sr-82 and Sr-85 the following experiment was performed.

On day 1 a typical generator column was loaded with 2.3 GBq Sr-82. The generator was eluted repeatedly with phosphate buffered saline (PBS) at pH=7.4. On day 26 and at an elution volume of 3.2 liter the generator was reloaded with 2.2 GBq Sr-82. Again, the generator was eluted repeatedly with PBS. On day 66 and at a total elution volume of 6.3 liter the generator was reloaded for a second time with 1.2 GBq Sr-82. Again, the generator was eluted repeatedly with PBS (pH=7.4). The total elution volume was 7.9 liter.

Figure 4:
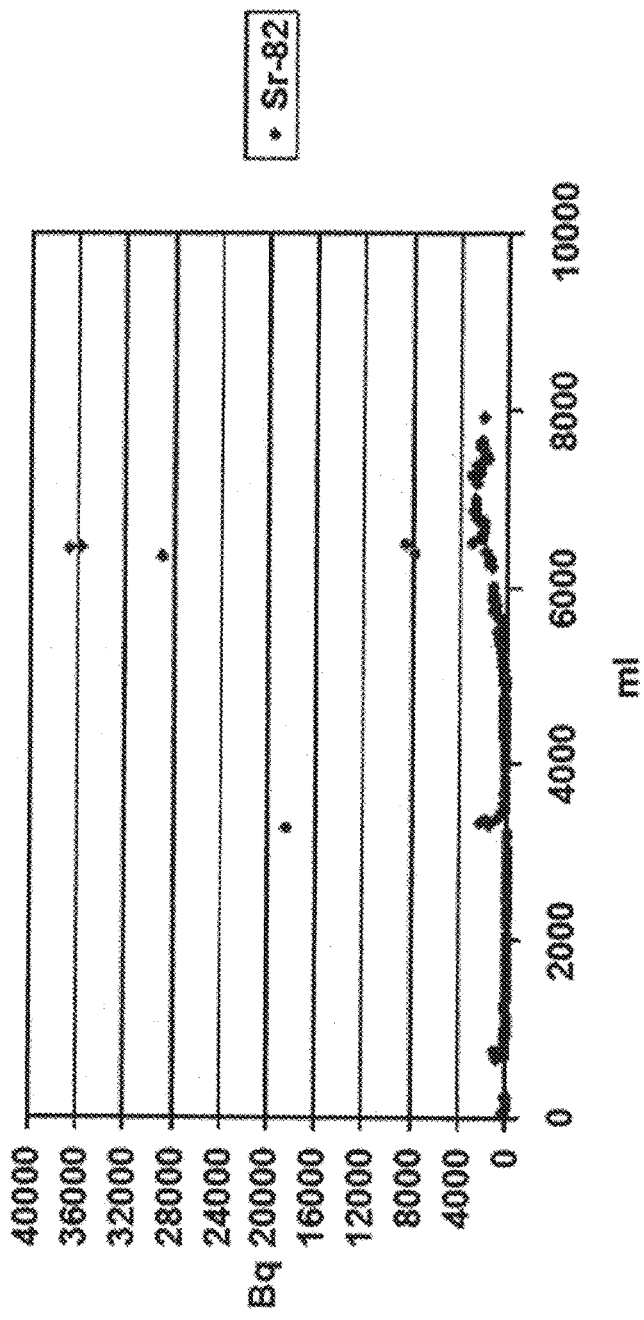
FIG. 4 shows the contamination of Sr-82 in the generator's eluate.
Figure 5:
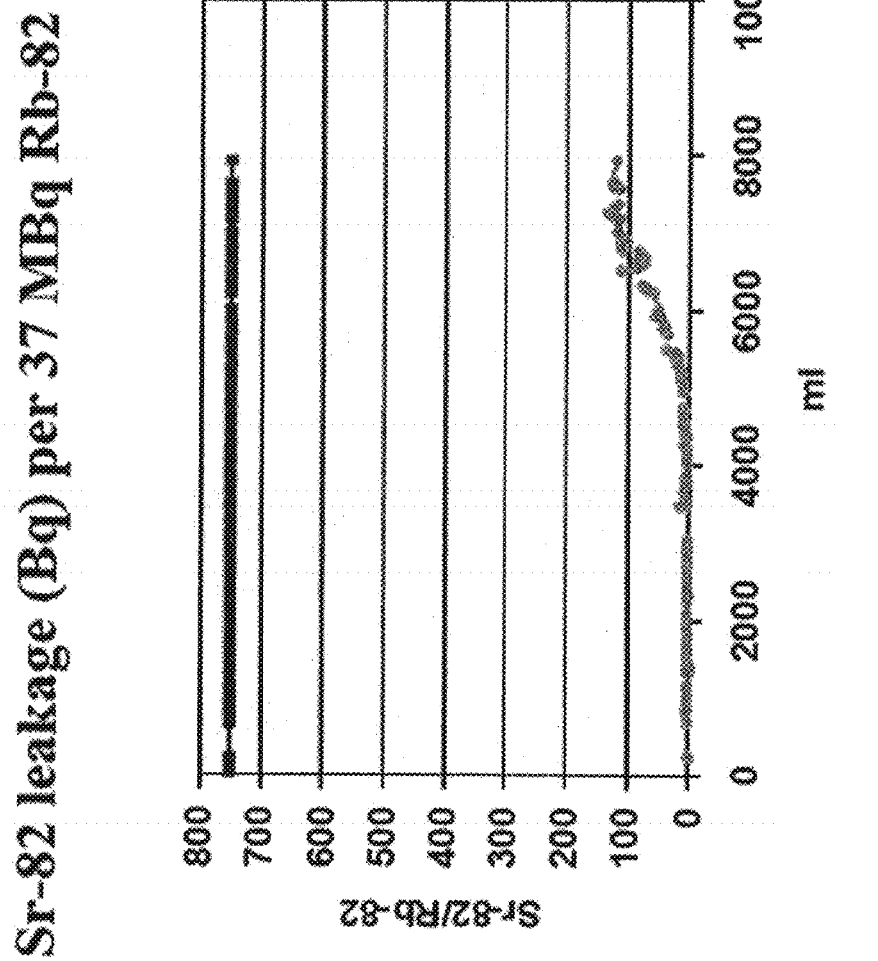
FIG. 5 shows the contamination of Sr-82 in the eluates expressed as Bq Sr-82 per MBq Rb-82.
Figure 6:
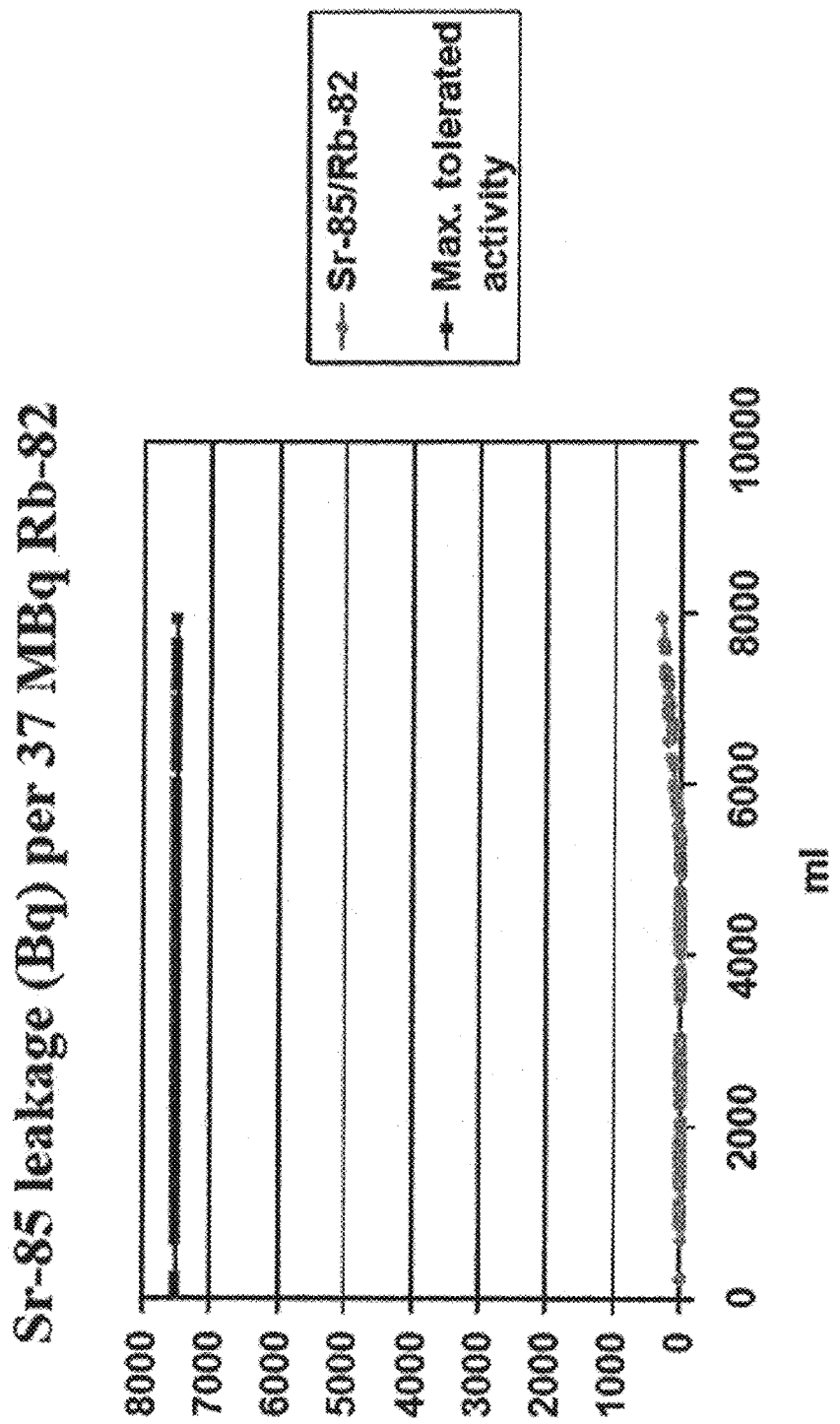
FIG. 6 shows the contamination of Sr-85 in the eluates expressed as Bq Sr-85 per MBq Rb-82.

FIG. 4 represents the contamination of Sr-82 in the generator's eluate. The curve spikes represent the moments of reloading. FIG. 5 shows the contamination of Sr-82 in the eluates (lower curve) expressed as Bq Sr-82 per 37 MBq Rb-82 and the maximal contamination of Sr-82 (higher curve) acceptable in the currently commercially available Rb-82 generators (Bracco). The level of contamination of Sr-82 is well below the acceptable contamination in the known generators. FIG. 6 shows the contamination of Sr-85 in the eluates (lower curve) expressed as Bq Sr-85 per 37 MBq Rb-82 and the maximal contamination of Sr-85 (higher curve) acceptable in currently commercially available Rb-82 generators (Bracco). The level of contamination of Sr-82 is well below the acceptable contamination in the known generators.

After three loadings and an elution volume of approximately 8 liters the contaminations of Sr-82 and Sr-85 are still far below the limit. Reloading a Sr-85/Rb-82 generator is of advantage because it reduces costs for Sr-82 by 30% and makes the transport of the generator back to the factory unnecessary.

The invention claimed is:

1. A strontium-82/rubidium-82 generator, the generator comprising:
   a column filled with a cationic exchanger loaded with strontium-82, and having an inlet and an outlet;
   an elution medium for rubidium-82, wherein the elution medium is a physiological buffer having a pH ranging from 6 to 8.5; and
   a sterilization medium comprising a suitable concentration of hypochlorite such that the generator can be used for 2 to 6 months at a substantially constant stability,
   wherein the parts of the column, the inlet and the outlet that come into contact with the elution medium are made of polyetheretherketone (PEEK).

2. The generator according to claim 1, wherein the physiological buffer is a carbonate buffer, a phosphate buffer or a Tris buffer.

3. The generator according to claim 1, wherein the cationic exchanger has been reloaded at least one time with strontium-82.

4. The generator according to claim 3, wherein the cationic exchanger has been reloaded at least twice with strontium-82.

5. The generator according to claim 1, wherein the cationic exchanger is a tin oxide.

6. The generator according to claim 1, wherein the physiological buffer has a pH ranging from 7 to 8.

7. The generator according to claim 1, wherein the physiological buffer has a pH ranging from 7.2 to 7.4.

8. The generator according to claim 1, wherein the sterilization medium has a suitable concentration of hypochlorite such that the generator can be used for 1 to 4 months at a substantially constant stability.

9. The generator according to claim 1, wherein the concentration of hypochlorite in the sterilization medium is 0.05%.

10. A strontium-82/rubidium-82 generator, the generator comprising:
    a column filled with a cationic exchanger loaded with strontium-82, and having an inlet and an outlet;
    an elution medium for rubidium-82, wherein the elution medium is a physiological buffer having a pH ranging from 6 to 8.5;
    a sterilization medium comprising a suitable concentration of hypochlorite such that the generator can be used for 2 to 6 months at a substantially constant stability,
    wherein the parts of the column, the inlet and the outlet that come into contact with the elution medium are made from polyetheretherketone (PEEK);
    a source for the elution medium;
    a source for the sterilization buffer;
    a pump for connecting and transporting the elution medium source to the inlet of the column;
    a dose calibrator connected to the outlet of the column; and
    a patient administration line connected to the dose calibrator.

11. The generator according to claim 10, arranged on a mobile vehicle.

12. The generator according to claim 10, wherein the cationic exchanger has been reloaded at least one time with strontium-82.

13. The generator according to claim 12, wherein the cationic exchanger has been reloaded at least twice with strontium-82.

14. The generator according to claim 10, wherein the sterilization medium has a suitable concentration of hypochlorite such that the generator can be used for 1 to 4 months at a substantially constant stability.

* * * * *